United States Patent [19]
Kirkpatrick

[11] 4,205,177
[45] May 27, 1980

[54] CARBAMYLTRIAZOLE INSECTICIDES

[75] Inventor: Joel L. Kirkpatrick, Overland Park, Kans.

[73] Assignee: Gulf Oil Corporation, Pittsburgh, Pa.

[21] Appl. No.: 839,695

[22] Filed: Oct. 5, 1977

Related U.S. Application Data

[62] Division of Ser. No. 662,496, Mar. 1, 1976, Pat. No. 4,160,839.

[51] Int. Cl.$^2$ .......................................... C07D 249/12
[52] U.S. Cl. .................................................. 548/265
[58] Field of Search ...................... 260/308 R; 548/265

[56] References Cited

U.S. PATENT DOCUMENTS

| | | | |
|---|---|---|---|
| 3,308,131 | 3/1967 | McKusick | 260/308 R |
| 3,952,001 | 4/1976 | Brookes et al. | 260/293.69 |
| 4,054,664 | 10/1977 | Watkins et al. | 260/308 R |

*Primary Examiner*—Alton D. Rollins
*Attorney, Agent, or Firm*—Carl A. Cline

[57] ABSTRACT

Insects of the orders Diptera, Coleoptera, Orthoptera and Lepidoptera are killed in the presence of living plants by applying to the locus of the insects an effective amount of a compound having the structural formula

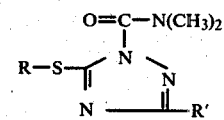

in which R is 2-propynyl, allyl, 2-bromoallyl, 2-chloroallyl, 2-methylallyl, 1-methylallyl or 2,3,3-trichloroallyl and R' is tert.butyl, propyl, cyclopropyl, isopropyl or 1-methylpropyl.

6 Claims, No Drawings

CARBAMYLTRIAZOLE INSECTICIDES

This is a division of U.S. Ser. No. 662,496, filed Mar. 1, 1976, now U.S. Pat. No. 4,160,839.

DESCRIPTION OF THE INVENTION

Background of the Invention

U.S. Pat. No. 3,308,131 discloses a class of compounds, said to be useful as insecticides, having the general structural formula

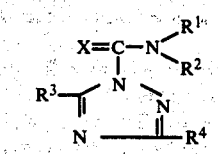

Compounds in which there is aliphatic unsaturation in $R^3$ or $R^4$ are specifically excluded from the disclosed class. It is true that some of the specifically excluded compounds are virtually useless as insecticides. One example is the compound 1-N,N-dimethylcarbamyl-3-cyclohexyl-5-propargylthio-1,2,4-triazole. Similar compounds with a trifluoromethyl substituent in 3- position are also generally lacking in insecticidal activity of any practical importance.

However, I have discovered a restricted group of highly active, useful insecticides among those excluded from the aforementioned patent which have the general structural formula

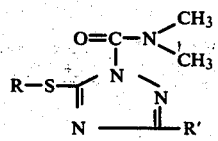

in which R is 2-propynyl, allyl, 2-bromoallyl, 2-chloroallyl, 2-methylallyl, 2,3,3-trichloroallyl, or 1-methylallyl and R' is tert.butyl, propyl, cyclopropyl, isopropyl or 1-ethylpropyl.

Summary of Invention

Briefly, my invention is the method of selectively killing insects of the orders Diptera, Coleoptera, Orthoptera and Lepidoptera in the presence of living plants comprising applying to the locus of the insects an effective amount of a compound having the structural formula

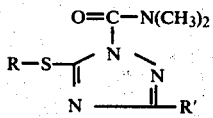

in which R is 2-propynyl, allyl, 2-bromoallyl, 2-chloroallyl, 2-methylallyl, 1-methylallyl or 2,3,3-trichloroallyl and R' is tert.butyl, propyl, cyclopropyl, isopropyl or 1-methylpropyl. The methods of manufacturing and use of the novel insecticides are illustrated specifically in the detailed description which follows.

DETAILED DESCRIPTION

The insecticide is conveniently prepared on a laboratory scale by means of the procedures described below.

Preparation of 3-tert.butyl-4H-1,2,4-triazolin-5-thione

To a suspension of 50 g (0.55 mol) of thiosemicarbazide and 43 g (0.05 mol) of pyridine in 300 ml of dioxane was added 42.6 g (0.6 mol) of pivalyl chloride, with cooling. The reaction was stirred at room temperature for 72 hours, then poured into water. The resulting solid was collected, washed with water and dried. The unpurified pivalyl thiosemicarbazide was heated at reflux temperature in 300 ml of 10% sodium hydroxide solution for 3 hours. After cooling, the pH was adjusted to 4 with hydrochloric acid and the product collected, washed with water and dried to give 43.8 g, m.p. 200°–203°. Recrystallization from methanol-chloroform solvent mixture gave a sample, m.p. 203°–205°.

Preparation of 3-tert.butyl-5-allylthio-4H-1,2,4-triazole

To a suspension of 150 g (0.955 mol) of 3-tert.butyl-4H-1,2,4-triazolin-5-thione in 1000 ml of ethanol was added 121 g (1.0 mol) of allyl bromide. After stirring at room temperature for 16 hrs, the reaction was heated at reflux temperature for two hrs, then most of the ethanol was removed at reduced pressure on the rotary evaporator. Water was added to dissolve the precipitated solids and the solution was taken to pH 9 with dilute $NH_4OH$. The product precipitated and was collected, giving 156.8 g, m.p. 127°–130°. Recrystallization from ether-petroleum ether solvent mixture raised the melting point to 131°–133°.

Preparation of 1-Dimethylcarbamyl-3-tert.butyl-5-allylthio-1H-1,2,4-triazole A solution of 56 g (0.284 mol) of 3-tert.butyl-5-allylthio-4H-1,2,4-triazole and 31.2 g (0.29 mol) of dimethylcarbamyl chloride in 300 ml of pyridine was maintained at reflux temperature for 16 hrs. After the pyridine was removed at reduced pressure on the rotary evaporator, water was added followed by chloroform. The organic layer was washed with successive portions of dilute hydrochloric acid, water and brine, then dried over $Na_2SO_4$. The solvent was removed in vacuo to give 66.3 g of an oil, $n_D^{26}$ 1.5126.

The compounds disclosed specifically below, as well as other compounds of the class of the invention may be made from purchased raw materials by means of the general procedures which are specifically exemplified above.

Use of the Novel Insecticides

Use of the new insecticide is illustrated by means of controlled tests providing a measure of efficacy on various species, according to procedures described below.

Method for Mites, Aphids, Bean Beetles and Army Worms

Three 5 oz paper cups containing Henderson dwarf lima bean plants and one 5 oz paper cup containing Orange Gem nasturtiums, all growing in vermiculite, are placed on a turntable and sprayed to thorough wetness with 25 ml of a solution of the candidate chemical at the appropriate concentration. Nasturtiums were already infested with 50–100 bean aphids (BA). A bean plant in one paper cup was already infested with 50-100 two-spotted mites (TSM). Leaves from the two remaining bean plants are removed following spraying and placed in disposable perti dishes with 5 southern armyworm (SA) larvae in one petri dish, and 5 Mexican bean beetle (MBB) larvae in the other petri dish. The rating is done approximately 48 hours after spraying as follows:

| BA | TSM |
|---|---|
| 0 = none dead | 0 = no dead adults |
| 1 = 1-25% dead | 1 = 1-25% dead adults |
| 2 = 26-50% dead | 2 = 26-50% dead adults |
| 3 = 51-75% dead | 3 = 51-75% dead adults |
| 4 = 76-99% dead | 4 = 76-99% dead adults |
| 5 = 100% dead | 5 = 100% dead adults |

| MBB | SA |
|---|---|
| 0 = no larvae dead | 0 = no larvae dead |
| 1 = 1-25% larvae dead | 1 = 1-25% larvae dead |
| 2 = 26-50% larvae dead | 2 = 26-50% larvae dead |
| 3 = 51-75% larvae dead | 3 = 51-75% larvae dead |
| 4 = 76-99% larvae dead | 4 = 76-99% larvae dead |
| 5 = 100% larvae dead | 5 = 100% larvae dead |

Method for Southern Corn Rootworm (SCR)

Three 5 oz paper cups planted each with one kernel of DeKalb XL-361 corn are treated two days after planting with 10 ml of a 125 ppm solution of the candidate compound. Compounds with high efficacy are treated at lower concentrations. The experiment is a 4×5 factorial in a randomized complete block design with three replications. The tests are evaluated nine days after treatment. The roots are inspected under a dissecting microscope and rated as follows:

| SCR Rating | % root feeding damage |
|---|---|
| 5 | 0 |
| 4 | 1-25 |
| 3 | 26-50 |
| 2 | 51-75 |
| 1 | 76-99 |
| 0 | 100 |

So as to obtain more meaningful results, all tests are performed at the same time of day, whenever possible, usually in the forenoon. Temperature, illumination and humidity are the same in all tests. Atmospheric pressure is not controlled.

Results obtained with the novel insecticides of this invention concentrations of active chemical are tabulated below. The ratings given are for averages of three or more replicates. The oral lethal dose for 50 percent kill of laboratory rats is also recorded in the table. In conducting the toxicity tests on rats, 0.01 g of active chemical per ml in corn oil is employed as an additive to the diet of the animals.

RESULTS OF INSECTICIDAL USE OF COMPOUNDS OF THE FORMULA

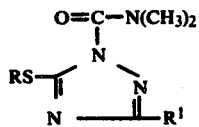

| Compound | Phys. properties | Species | 500 | 250 | 125 | 100 | 62 | 50 | 31 | 25 | 15 | 12 | 8 | 6 | 4 | 3 | 2 | Remarks |
|---|---|---|---|---|---|---|---|---|---|---|---|---|---|---|---|---|---|---|
| R = 2-propynyl (propargyl) R' = cyclopropyl | $n_D^{26}$ = 1.5585 | MBB | 5 | 5 | 5 | | 3 | | 1 | | 1 | | | | | | | |
| | | SA | 5 | 4 | 2 | | 0 | | 0 | | 0 | | | | | | | |
| | | BA | 5 | 5 | 5 | | 5 | | 5 | | 5 | | 5 | | 3 | | 1 | $LD_{50}$ 10 mg/kg |
| | | TSM | 5 | 4 | 4 | | 2 | | 0 | | 0 | | | | | | | |
| | | SCR | | | | 4.3 | | 4.3 | | 1.3 | | 0 | | 0 | | 0 | | |
| R = 2-propynyl R' = isopropyl | $n_D^{26}$ = 1.5286 | MBB | 5 | 5 | 5 | | 5 | | 4 | | 0 | | | | | | | |
| | | SA | 5 | 5 | 3 | | 0 | | 0 | | 0 | | | | | | | |
| | | BA | 5 | 5 | 5 | | 5 | | 5 | | 5 | | 2 | | 3 | | 0 | $LD_{50}$ approx. 50 mg/kg |
| | | TSM | 0 | | | | | | | | | | | | | | | |
| | | SCR | | | | 4 | | 2.7 | | 1.3 | | 0.3 | | 0 | | 0 | | |
| R = 2-propynyl R' = propyl | $n_D^{26}$ = 1.5242 | MBB | 5 | 5 | 5 | | 3 | | 1 | | 0 | | | | | | | |
| | | SA | 5 | 0 | 0 | | 0 | | 0 | | 0 | | | | | | | |
| | | BA | 5 | 5 | 5 | | 5 | | 5 | | 5 | | 1 | | 0 | | 0 | |
| | | TSM | 0 | | | | | | | | | | | | | | | |
| | | SCR | | | | 3.7 | | 2.7 | | 1.3 | | 0 | | 0 | | 0 | | |
| R = 2-bromopropenyl (2-bromoallyl) R' = cyclopropyl | $n_D^{26}$ = 1.5455 | MBB | 2 | | | | | | | | | | | | | | | |
| | | SA | 0 | | | | | | | | | | | | | | | |
| | | BA | 5 | 5 | 5 | | 5 | | 4 | | 2 | | 0 | | | | | |
| | | TSM | 2 | | | | | | | | | | | | | | | |
| | | SCR | | | | 4.3 | | 0.3 | | 0 | | 0 | | 0 | | 0 | | |
| R = 2-propenyl (allyl) R' = tert.butyl | $n_D^{26}$ = 1.5126 | MBB | 5 | 5 | 5 | | 1 | | 0 | | 0 | | | | | | | |
| | | SA | 1 | | | | | | | | | | | | | | | |
| | | BA | 5 | 5 | 5 | | 5 | | 5 | | 5 | | 4 | | 3 | | 2 | $LD_{50}$ 17 mg/kg |
| | | TSM | 0 | | | | | | | | | | | | | | | |
| | | SCR | | | | 4 | | 3 | | 2.5 | | | | 1 | | | | |
| R = 2-propynyl R' = tert.butyl | $n_D^{26}$ = 1.5212 | MBB | 5 | 5 | 5 | | 5 | | 5 | | 4 | | 0 | | 0 | | | |
| | | SA | 5 | 5 | 2 | | 0 | | 0 | | 0 | | | | | | | |
| | | BA | 5 | 5 | 5 | | 5 | | 5 | | 5 | | 5 | | 5 | | | $LD_{50}$ > 50 mg/kg |
| | | TSM | 1 | | | | | | | | | | | | | | | |
| | | SCR | | | | 4 | | 5 | | 5 | | 4.5 | | 3.5 | | 2 | | |
| R = 2-bromo-2-propenyl (2-bromoallyl) R' = tert.butyl | m.p. 52°-56° C. | MBB | 2 | | | | | | | | | | | | | | | |
| | | SA | 0 | | | | | | | | | | | | | | | |
| | | BA | 5 | 5 | 5 | | 5 | | 5 | | 5 | | 4 | | 4 | | | |
| | | TSM | 4 | 0 | 0 | | 0 | | 0 | | 0 | | | | | | | |
| | | SCR | | | | 0 | | | | | | | | | | | | |
| R = 2-propenyl (allyl) | $n_D^{26}$ = 1.5175 | MBB | 5 | 5 | 5 | | 2 | | 0 | | 0 | | | | | | | |
| | | SA | 5 | 0 | 0 | | 0 | | 0 | | 0 | | | | | | | $LD_{50}$ between |

RESULTS OF INSECTICIDAL USE OF COMPOUNDS OF THE FORMULA

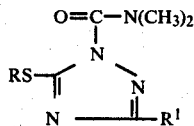

| Compound | Phys. properties | Species | 500 | 250 | 125 | 100 | 62 | 50 | 31 | 25 | 15 | 12 | 8 | 6 | 4 | 3 | 2 | Remarks |
|---|---|---|---|---|---|---|---|---|---|---|---|---|---|---|---|---|---|---|
| R' = isopropyl | | BA | 5 | 5 | 5 | | 5 | | 5 | | 5 | | 4 | | 2 | | 0 | 10 and 50 mg/kg |
| | | TSM | 0 | | | | | | | | | | | | | | | |
| | | SCR | | | | 4 | | 4 | | 4 | | 4 | | 4 | | 3.5 | | | |
| R = 2-propenyl | | MBB | 5 | 5 | 2 | | 0 | | 0 | | 0 | | | | | | | |
| (allyl) | $n_D^{26} = 1.5373$ | SA | 5 | 0 | 0 | | 0 | | 0 | | 0 | | | | | | | LD$_{50}$ between |
| R' = cyclopropyl | | BA | 5 | 5 | 5 | | 5 | | 5 | | 5 | | 5 | | 5 | | 4 | 5 and 10 mg/kg |
| | | TSM | 5 | 5 | 5 | | 3 | | 0 | | 0 | | | | | | | |
| | | SCR | | | | 5 | | 3.5 | | 3.0 | | 2.5 | | 2.5 | | 3.0 | | | |
| R = 2-methylallyl | liquid | MBB | 2 | | | | | | | | | | | | | | | |
| R' = tert.butyl | | SA | 0 | | | | | | | | | | | | | | | |
| | | BA | 5 | 5 | 5 | | 5 | | 5 | | 5 | | 4 | | 4 | | 1 | |
| | | TSM | 0 | | | | | | | | | | | | | | | |
| | | SCR | | | | 1.3 | | | | | | | | | | | | |
| R = 2-chloroallyl | liquid | MBB | 2 | | | | | | | | | | | | | | | |
| R' = tert.butyl | | SA | 0 | | | | | | | | | | | | | | | |
| | | BA | 5 | 5 | 5 | | 5 | | 5 | | 5 | | 4 | | 4 | | 4 | |
| | | TSM | 0 | | | | | | | | | | | | | | | |
| | | SCR | | | | 1 | | | | | | | | | | | | |
| R = 2,3,3-trichloroallyl | | MBB | 0 | | | | | | | | | | | | | | | |
| | m.p. 62°–67° | SA | 0 | | | | | | | | | | | | | | | |
| R' = tert.butyl | | BA | 4 | 5 | 5 | | 5 | | 5 | | 5 | | 4 | | 3 | | 3 | |
| | | TSM | 0 | | | | | | | | | | | | | | | |
| | | SCR | | | | | | | | | | | | | | | | |
| R = 1-methylallyl | liquid | MBB | 5 | 1 | 1 | | 0 | | 0 | | 0 | | | | | | | |
| R' = tert.butyl | | SA | 4 | 0 | 0 | | 0 | | 0 | | 0 | | | | | | | |
| | | BA | 5 | 5 | 5 | | 5 | | 5 | | 5 | | | | | | | |
| | | TSM | 0 | | | | | | | | | | | | | | | |
| | | SCR | | | | | | | | | | | | | | | | |

It will be realized by workers in the art that the efficacy of the insecticides at low concentration levels makes it advisable to combine the compounds with inert carriers, according to conventional practice. In this way the compounds may be distributed more uniformly at desired concentration levels. Water is the most convenient inert carrier in many situations and it is conventional practice to use commercial emulsifiers and dispersing agents so as to easily obtain uniform dispersions in water for spray application. For use against soilborne insects, dry granular combinations of insecticides with solid inert carriers may be preferred, according to the common practice in the art.

It is only necessary to apply the insecticides to the zone in which the insects live, or locus of the insects. Normal activity of the insects will assure adequate contact with the insecticides, so that they need not be applied directly to the insects.

I claim:

1. 1-(N,N-Dimethylcarbamyl)-3-cyclopropyl-5-(2-propynylthio)-1H-1,2,4-triazole.
2. 1-(N,N-Dimethylcarbamyl)-3-propyl-5-(2-propynylthio)-1H-1,2,4-triazole.
3. 1-(N,N-Dimethylcarbamyl)-3-cyclopropyl-5-(2-bromoallylthio)-1H-1,2,4-triazole.
4. 1-(N,N-Dimethylcarbamyl)-3-tert.-butyl-5-allylthio-1H-1,2,4-triazole.
5. 1-(N,N-Dimethylcarbamyl)-3-isopropyl-5-allylthio-1H-1,2,4-triazole.
6. 1-(N,N-Dimethylcarbamyl)-3-cyclopropyl-5-allylthio-1H-1,2,4-triazole.

* * * * *